(12) United States Patent
Letort et al.

(10) Patent No.: US 6,669,647 B2
(45) Date of Patent: Dec. 30, 2003

(54) SENSING DEVICE AND METHOD FOR DETERMINING ANEURYSMAL PRESSURE IN A BODY CAVITY

(75) Inventors: Michel Letort, Larkspur, CA (US); David Tseng, Santa Rosa, CA (US)

(73) Assignee: Medtronic AVE, Inc., Santa Rosa, CA (US)

( * ) Notice: Subject to any disclaimer, the term of this patent is extended or adjusted under 35 U.S.C. 154(b) by 0 days.

(21) Appl. No.: 10/128,957

(22) Filed: Apr. 23, 2002

(65) Prior Publication Data

US 2003/0199772 A1 Oct. 23, 2003

(51) Int. Cl.[7] .......................... A61B 5/02; A61B 5/103; A61B 5/117
(52) U.S. Cl. ........................ 600/486; 600/488; 600/481; 600/587
(58) Field of Search ................................ 600/486, 587, 600/485, 481, 483, 300, 488

(56) References Cited

U.S. PATENT DOCUMENTS

| 3,631,850 | A | 1/1972 | Levasseur |
|---|---|---|---|
| 4,226,124 | A | 10/1980 | Kersten |
| 4,610,256 | A | 9/1986 | Wallace |
| 5,607,464 | A | 3/1997 | Trescony et al. |
| 6,143,022 | A | 11/2000 | Shull et al. |
| 6,159,156 | A | 12/2000 | Van Bockel |
| 6,309,350 | B1 | 10/2001 | Van Tassel |

FOREIGN PATENT DOCUMENTS

EP  0 114 239 A2  1/1984

*Primary Examiner*—Max F. Hindenburg
*Assistant Examiner*—Navin Natnithithadha
(74) *Attorney, Agent, or Firm*—Janis J. Biksa

(57) ABSTRACT

A device for sensing aneurysmal pressure in a body cavity includes a housing including at least one chamber formed therein. A first fluid is positioned in a first portion of the chamber. A second fluid is positioned in a second portion of the chamber. A compressible fluid is positioned in the second portion of the chamber. A divider is positioned between the first and second fluids. A pressure membrane is in communication with the first portion of the chamber. The aneurysmal pressure is transmitted through the membrane and the first fluid to position the divider within the chamber. A method for determining aneurysmal pressure in a body cavity includes deploying a sensing device including radiopaque substance adjacent an aneurysm. The radiopaque substance is moved within the device in response to the aneurysmal pressure. The sensing device is imaged and pressure and/or relative pressure is read directly.

22 Claims, 6 Drawing Sheets

SENSING DEVICE AND METHOD FOR DETERMINING ANEURYSMAL PRESSURE IN A BODY CAVITY

FIELD OF THE INVENTION

The present invention relates generally to the field of implantable medical devices. More particularly, the invention relates to a sensing device and method for determining aneurismal pressure in a body cavity.

BACKGROUND OF THE INVENTION

Vascular aneurysms are produced when a thinning or weak spot in a vessel wall dilates eventually posing a health risk from its' potential to rupture, clot, or dissect. While aneurysms can occur in any blood vessel, most occur in the aorta and peripheral arteries. The majority of aortic aneurysms occur in the abdominal aorta, usually beginning below the renal arteries and often extending into one or both of the iliac arteries. The etiology of aneurysm formation is not entirely understood, but is thought to be related to congenital thinning of the artery, atherosclerotic vessel degeneration, vessel trauma, infection, smoking, high blood pressure, and other causes leading to vessel degeneration. Left untreated, aneurysms may lead to gradual vessel expansion, thrombus formation leading to stroke or other vessel blockage, vessel rupture, shock, and eventual death.

Aneurysms may be treated in open surgical procedures, where the diseased vessel segment is bypassed and repaired with an artificial vascular graft. While considered to be an effective surgical technique, particularly considering the alternative of the usually fatal ruptured aneurysm, conventional vascular graft surgery suffers from a number of disadvantages. The surgical procedure is complex and requires experienced surgeons and well equipped surgical facilities. Even with the best surgeons and equipment, patients suffering from such aneurysms are often elderly and weakened from cardiovascular and other diseases. This factor reduces the number of patients eligible for surgery. Even for eligible patients prior to rupture, conventional aneurysm repair has a relatively high mortality rate, usually from 2 to 10%. Morbidity related to the conventional surgery includes myocardial infarction, renal failure, impotence, paralysis, and other conditions. Even with successful surgery, recovery takes several weeks and often requires a lengthy hospital stay.

To overcome some of the drawbacks associated with open surgery, a variety of endovascular prosthesis placement techniques have been proposed. Without the need for open surgery, patient complications and recovery time may be significantly reduced. The most common type of aneurysm, the abdominal aortic aneurysm (AAA) may be used as an example for treatment with a prosthetic device. For example, one endovascular AAA repair technique involves a tubular prosthesis deployed by remote insertion through a femoral artery. A stent-graft prosthesis permits a sealed shunt of blood flow from a healthy portion of the aorta, through the aneurysm, and into one or both of the iliac artery branches. The prosthesis excludes any thrombus present in the aneurysm while providing mechanical reinforcement of the weakened vessel reducing the risk of dissection and rupture, respectively. Furthermore, the prosthesis can substantially reduce the blood pressure within the isolated aneurysmal sac providing the weakened vessel with a favorable healing environment. Backflow from blood vessels in communication with the aneurismal sac may continue to pressurize the, aneurysm despite the presence of a shut.

A known shortcoming of some of the implantable endovascular prosthetics relates to migration and seal. The affected vessel(s) may vary widely in location, size, and the distended shape of the aneurysm itself. Particularly after treatment, the aneurysm and associated vessels may drastically change morphology thereby exerting stress forces on the deployed prosthesis. With sufficient change in aneurysm morphology and subsequent stress placed on the prosthesis, the device may migrate and/or detach from the vessel wall. As a result, the fluid seal may be compromised and blood may leak into the aneurysm from the aorta thereby elevating the aneurysmal pressure. The patient may have to undergo another treatment given the problem is detected early. The described or other undetected "endoleakage" may lead to aneurysm growth or regrowth, and to the more serious problems associated with aneurysms. Accordingly, it would be desirable to provide a strategy for monitoring an aneurysm.

Current strategies for monitoring aneurysms involve imaging by means of CT-scan magnetic resonance, angiography, duplex ultrasound, and the like. These imaging methods may utilize a contrast solution to enhance the visualization process. Some patients may be allergic to the iodine based solutions and other "dyes". In certain situations, the patient may experience a warm "flushed" sensation, a transient metallic taste, or a mild itching over various parts of the body with developing hives. In rare situations, the patient may suffer from a strong, sudden, and systemic response to the contrast solutions. Such anaphylactic responses may involve mental confusion, dizziness (due to a drop in blood pressure), swelling (especially of the face, tongue and throat), and difficulty breathing. The reactions can be more serious if not treated immediately. Therefore, it would be desirable to provide a strategy for monitoring an aneurysm without the use of appreciable volumes of contrast solution.

Another shortcoming of the aforementioned imaging strategies relates to sensitivity. Current methods may effectively visualize the size and shape of the aneurysm, providing a passive monitoring strategy. However, such methods may not effectively detect the presence of an endoleak. For example, the aneurysm may be largely filled with a thrombus. A sufficient amount of contrast solution may not be introduced into the aneurysm. This circumstance may lead to a reduced capacity in detecting endoleakage. Continued undetected endoleakage, even at a low level, may slow or even reverse the aneurysmal healing process. To avoid this and other situations where endoleakage cannot be detected, it may be more advantageous to measure endoleaks more directly. As such, it would be desirable to provide a strategy for directly measuring aneurysmal pressure.

Therefore, it would be desirable to provide a sensing device and method for determining aneurismal pressure that overcomes the aforementioned and other disadvantages.

SUMMARY OF THE INVENTION

One aspect according to the invention provides a device for sensing aneurysmal pressure in a body cavity. The device includes a housing including at least one chamber formed therein. A first fluid is positioned in a first portion of the chamber. A second fluid is positioned in a second portion of the chamber. A compressible fluid is positioned in the second portion of the chamber. A divider is positioned between the first and second fluids. A pressure membrane is in communication with the first portion of the chamber. The aneurysmal pressure is transmitted through the membrane and the first fluid to position the divider within the chamber. The body cavity may be an aorta. The first and second fluids may be non-miscible. At least one of the first and second fluids may include a biocompatible hydrocarbon and/or a radiopaque fluid. The radiopaque fluid may include barium sulfate, diatrizoate, iodipamide, iohexol, iopamidol, iothalamate, ioversol, ioxaglate, and metrizamide. The divider may be manufactured from a radiopaque material such as gold, silver, tantalum oxide, tantalum, platinum, platinum/iridium alloy, and tungsten. An anchor portion may be operably attached to the housing, wherein the anchor retains the housing adjacent the aneurysm. At least one gas may be positioned in the chamber, wherein the gas volume changes in response to the aneurysmal pressure. At least one radiopaque marker may be disposed on the housing. An endoluminal prosthesis may be positioned adjacent the aneurysm. A divider membrane may be positioned adjacent the compressible fluid and the second fluid, wherein the second fluid may be a liquid.

Another aspect according to the invention provides a method for determining aneurysmal pressure in a body cavity. The method includes deploying a sensing device including radiopaque substance adjacent an aneurysm. The radiopaque substance is moved within the device in response to the aneurysmal pressure. The sensing device is imaged. The body cavity may be an aorta. The sensing device may be deployed with a catheter. The sensing device may be retained adjacent the aneurysm. The sensing device may be imaged fluoroscopically. The sensing device may be calibrated. Calibration may include adjusting a radiopaque substance position with respect to a standard pressure and/or adjusting a rate of radiopaque substance movement with respect to the aneurysmal pressure before deployment. An endoluminal prosthesis may be deployed adjacent the aneurysm.

DETAILED DESCRIPTION

Figure 1A:
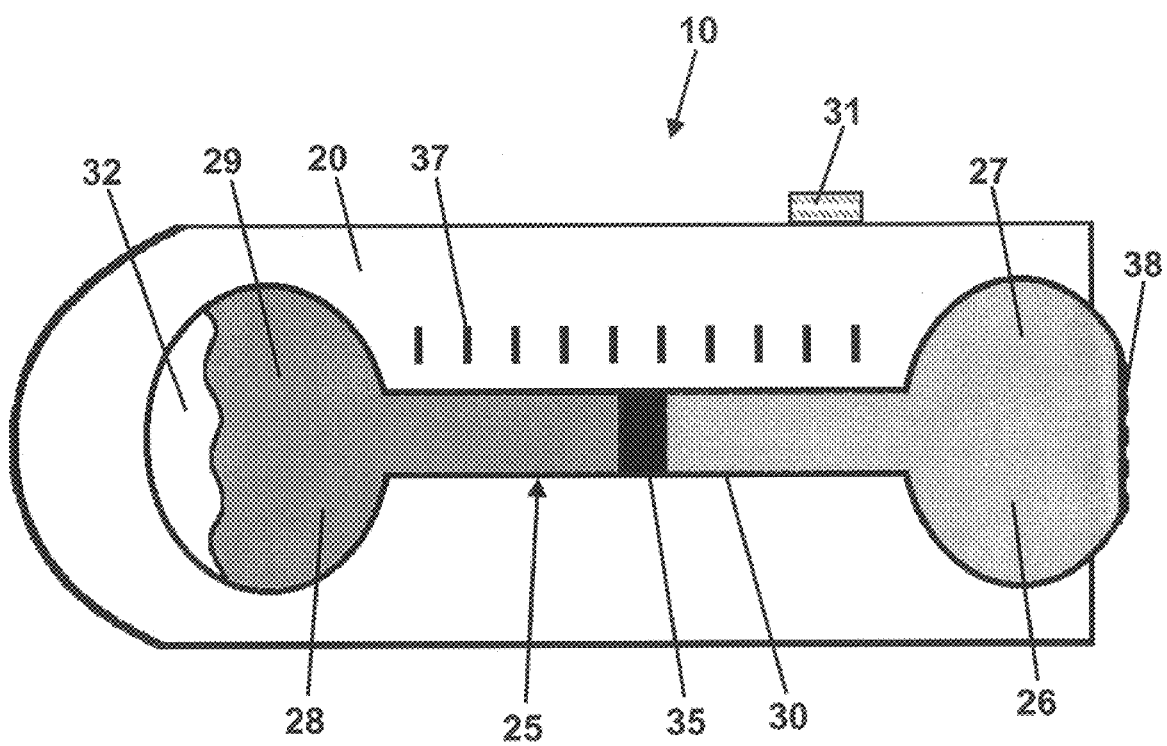
FIG. 1A is a cross-sectional side view of a device for sensing aneurysmal pressure, in accordance with the present invention.

Referring to the drawings, FIG. 1A is a cross-sectional view of a device 10 for sensing aneurysmal pressure in accordance with the present invention. Device 10 includes a housing 20 including at least one chamber 25 formed therein. The housing 20 may be manufactured substantially from a radiotransparent biocompatible material such as plastic, polymer, composite, or the like. Housing 20 may provide a fluid tight seal thereby isolating the chamber 25 from the external environment. In one embodiment, housing 20 may be substantially cylindrical with a length of about 10 to 40 mm, and width/height about 2 to 10 mm. In another embodiment, housing 20 geometry and dimensions may vary to suit a given application. For example, housing 20 may form a sphere, cylinder, cube, or irregular shape of various sizes and configurations.

A first fluid 26.is positioned in a first portion 27 of the chamber 25, and a second fluid 28 is positioned in a second portion 29 of the chamber 25. As shown in FIG. 1A, the chamber first portion 27 and second portion 29 may be roughly spherical in geometry. The chamber portions 27, 29 may extend into a connector portion 30, providing means for fluid communication there between. Those skilled in the art will recognize that the geometry and size of the chamber portions 27, 29 and connector portion 30 may vary without diminishing the utility of the present invention. As described below, the chamber portions 27, 29 and connector portion 30 geometries and sizes may be varied to adjust the function of the device 10.

At least one of the fluids 26, 28 may be radiopaque. The radiopaque fluid 26, 28 may include barium sulfate, diatrizoate, iodipamide, iohexol, iopamidol, iothalamate, ioversol, ioxaglate, metrizamide, and the like. Although the radiopaque fluid 26, 28 may be allergenic (e.g. iodine based contrast solution), a large volume need not be used with the present invention thereby reducing the risk to patient. The fluids 26, 28 may be non-miscible or miscible. In one embodiment, the first fluid 26 and second fluid 28 may be non-miscible. The use of non-miscible fluids 26, 28 may provide means for maintaining fluid separation. One of the first fluid 26 and second fluid 28 may be biocompatible hydrocarbon, such as liquid paraffins, lipids, glycerides, fatty acids, natural and synthetic hydrocarbons, and derivatives thereof. Such liquids are readily available from natural and synthetic sources. Several have been routinely used for consumption and/or delivery of pharmacological agents thereby demonstrating biocompatibility. Preferred natural hydrocarbons may include canola oil, soybean oil, olive oil, corn oil, castor oil, safflower oil and sunflower oil. The other fluid 26, 28 may be a biocompatible polar fluid such as a saline solution, thus being non-miscible with a hydrocarbon liquid. In another embodiment, the fluids 26, 28 may be miscible. For example, the fluids 26, 28 may have similar polarities or may be a like fluid. Those skilled in the art will recognize that the fluids 26, 28 may vary while still providing functionality with the present invention. The inventors contemplate numerous fluid 26, 28 compositions, combinations, and properties for use with the present invention.

A divider 35 is positioned between the fluids 26, 28. Divider 35 may be manufactured from a radiopaque material such as gold, silver, tantalum oxide, tantalum, platinum, platinum/iridium alloy, tungsten, and the like. Divider 35 may be adapted to slidably move within connector portion 30 and seal the chamber portions 27, 29 from one another. As such, divider 35 may maintain separation of the fluids 26, 28 by providing a moveable seal (e.g., may be required if both fluids 26, 28 are miscible). In one embodiment, divider 35 may have a cylindrical shape with a diameter slightly smaller than the connector portion. In another embodiment, divider 35 may have a spherical shape or other shape conforming to the connector portion 30 inner surface. Those skilled in the art will recognize that the geometry and size of the divider 35 may vary without diminishing the utility of the present invention.

An anchor portion 31 may be operably attached to the housing 20, wherein the anchor 31 retains the housing 20 adjacent an aneurysm. Anchor 31 may prevent migration of sensing device 10 from aneurysm. Anchor 31 may include any number of features used to secure a device to a vessel wall and/or to an endoluminal prosthesis. In one embodiment, anchor 31 may include a rigid barb or hook, such as those used for pacing leads, for attachment into a vessel wall. In another embodiment, anchor 31 may include sutures, latches, connectors, or adhesive for attachment to vessel wall or endoluminal prosthesis.

At least one radiopaque marker 37 may be disposed on the housing 20. Marker 37 may be manufactured from a radiopaque material such as that described for the divider 35. In one embodiment, as shown in FIG. 1A, a plurality of markers 37 may be arranged to provide a graduated index when visualized. In another embodiment, the marker(s) may include a variety of shapes, sizes, geometries, and arrangements to provide spatial information upon visualization. For example, two markers may be positioned a known distance (e.g., 5 mm) apart, providing a visual reference of other (radiopaque) objects visualized.

Figure 1B:
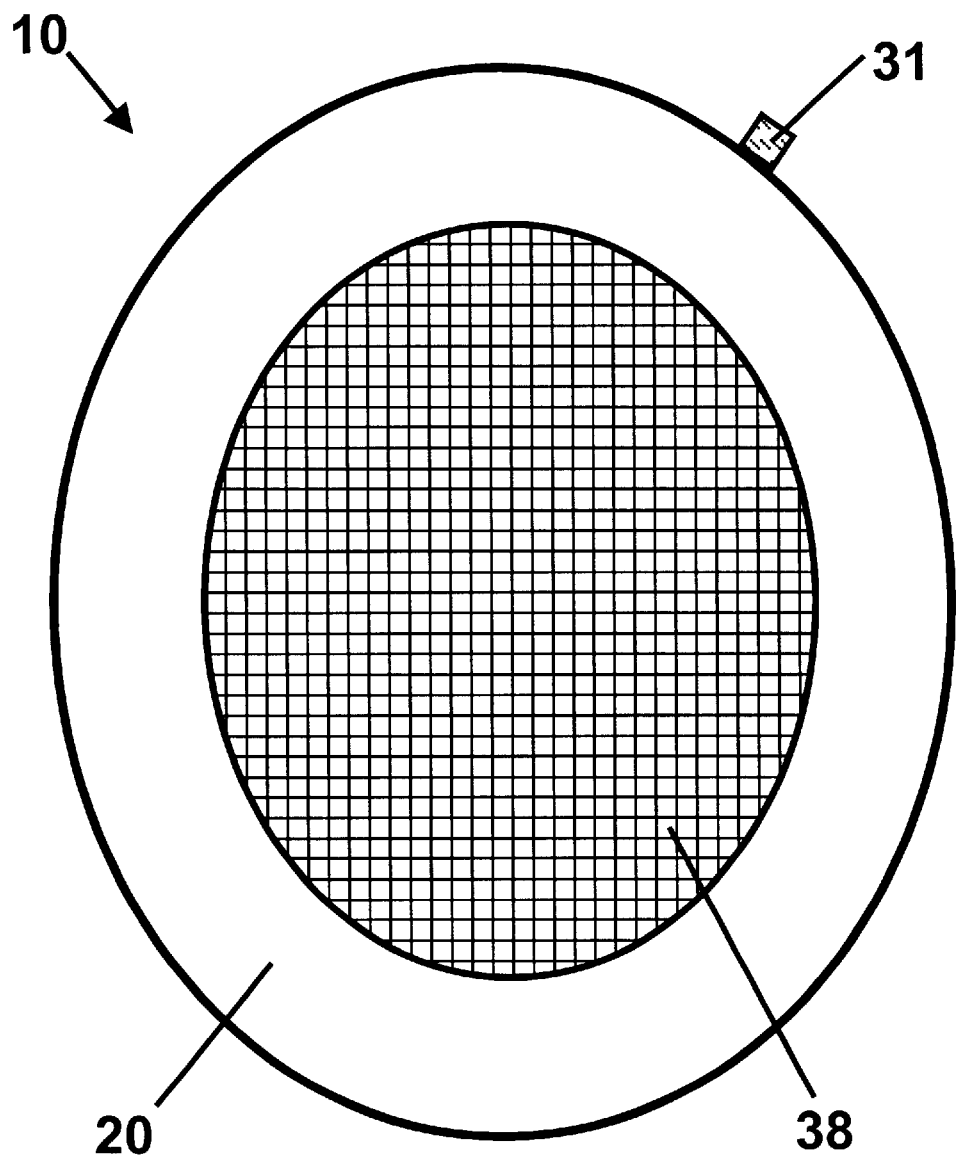
FIG. 1B is an end view of the device shown in FIG. 1A.

A pressure membrane 38 is in communication with the first portion 27 of the chamber 25. Pressure membrane 38 may be adapted to transmit external pressure to the first fluid 26. Pressure membrane may be manufactured from a pliable and biocompatible material such as a polymer, plastic, metallic or alloy foil, and the like. In one embodiment, as also shown in an end view (FIG.1B), pressure membrane 38 may be positioned adjacent chamber first portion 27 on an exterior surface of the pressure sensing device 10. In another embodiment, as described below, the pressure membrane 38 size, shape, and position may vary. Those skilled in the art will recognize that the numerous pressure membrane 38 configurations may be used with the present invention.

A compressible fluid is positioned in the chamber second portion 29 of the chamber 25. In one embodiment, the compressible fluid may be a gas. Referring again to FIG. 1A, a volume of gas 32 may be positioned in the chamber 25 second portion 29. Gas 32 may be a biocompatible gas such as nitrogen, air, or the like. Gas 32 volume may change in response to the aneurysmal pressure. During manufacture of the device 10, gas pressure may be adjusted to a desired pressure, to calibrate movement of divider 35. Adjusting the gas volume 32 pressure to an ambient pressure (e.g., 1 ATM) may minimize movement of divider 35 until device 10 is deployed and experiences pressure changes.

During operation of the sensing device 10, aneurysmal pressure exerted on membrane 38 is transmitted to first fluid 26 and on to the second fluid 28. The divider 35 moves (e.g., to the left in FIG. 1A) as the pressure moves second fluid 28 to compress gas volume 32 until pressure on both sides of pressure membrane 38 is equal. Subsequent changes in external pressure on the pressure membrane 38 may result in corresponding movement of the divider 35. For example, pressure increases results in divider 35 movement to the left whereas pressure decreases results in divider 35 movement to the right. Divider 35, fluid 26, 28, and/or marker 37 may then be imaged (e.g., by fluoroscopy) to determine aneurysm pressure. In one embodiment, divider 35 movements may be compared to marker 37 position to quantify pressure exerted on pressure membrane 38. For example, the divider 35 movement distance may be compared to a table or graph of known pressure to distance values to determine aneurysm pressure. In another embodiment, one or more radiopaque fluids 26, 28 may be visualized in addition to or in lieu of divider 35 to quantify pressure exerted on pressure membrane 38. For example, radiopaque fluid 26, 28 may move across connector portion 30. The movement of the radiopaque fluid 26, 28 and/or divider 35 may be compared to a graduated marker 37 index (e.g., similar to a thermometer) to determine relative aneurysmal pressure. Those skilled in the art will recognize that numerous strategies may be used to determine aneurysmal pressure with the present invention.

Determinations using the sensing device 10 may provide instantaneous reading of relative aneurysm pressure. Changes in aneurysm pressure such as what may occur by a patient moving from a standing to a sitting position may result in relatively quick movements in the fluid and divider. As such, when the aneurysm pressure is determined, it indicates the pressure at the time of imaging.

Numerous modifications, substitutions, and alterations may be made to the sensing device 10 without limiting the function of the invention. Such changes may allow the sensing device design to be adapted to various situations. In one embodiment, the sensitivity of the sensing device may be customized by differentially sizing the pressure membrane and/or connector portion. Sensitivity may influence degree of divider movement (e.g., greater sensitivity may provide increased movement of divider, and lower sensitivity may provide dampened movement of divider). In another embodiment, the housing and chamber geometry may be varied to provide alternative sensing device packaging. The sensing device packaging may be customized to physically "fit" a required application. For example, the sensing device housing may be sized to fit within a deployment catheter lumen, within the space of an aneurysm, etc.

Figure 2:
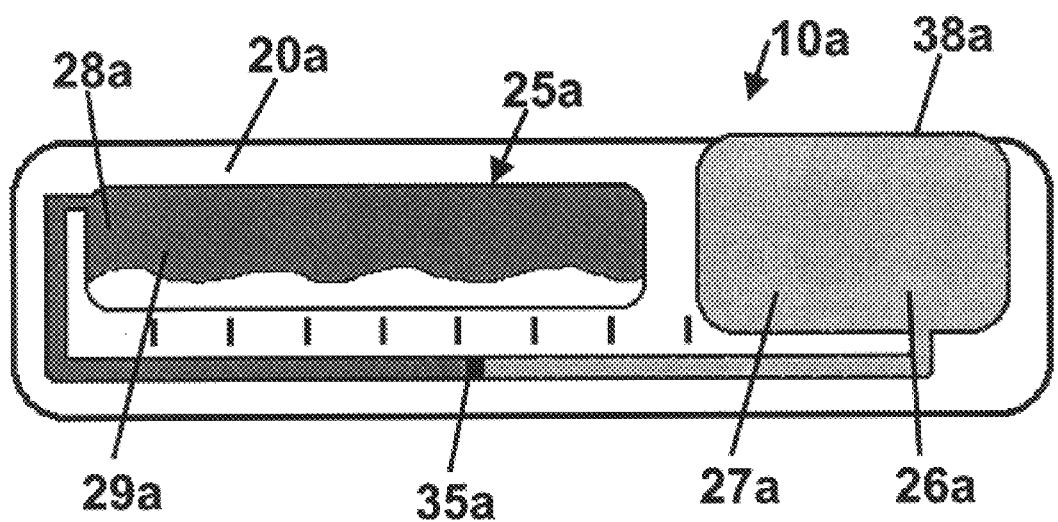
FIG. 2 is a cross-sectional view of a second device for sensing aneurysmal pressure, in accordance with the present invention.
Figure 3:
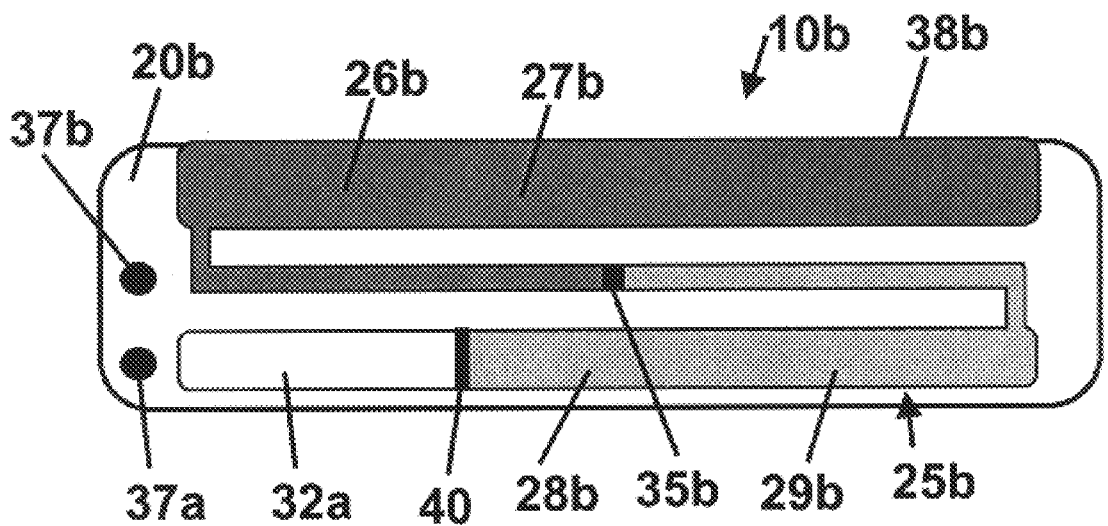
FIG. 3 is a cross-sectional view of a third device for sensing aneurysmal pressure, in accordance with the present invention.
Figure 4A:
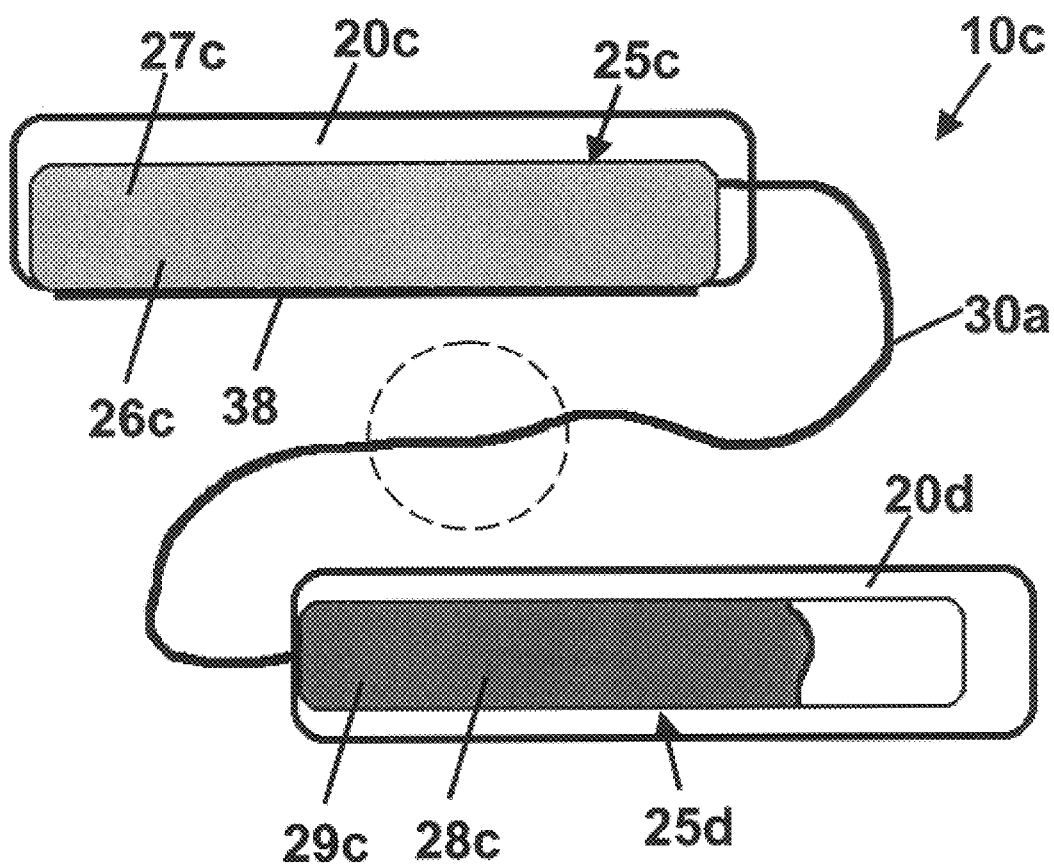
FIG. 4A is a cross-sectional view of a fourth device for sensing aneurysmal pressure, in accordance with the present invention.

Referring now to FIGS. 2, 3, and 4A cross-sectional views are provided of other embodiments of sensing devices 10a, 10b, 10c demonstrating several design variations. Sensing devices 10a, 10b, 10c includes: housing 20a, 20b, 20c; chamber 25a, 25b, 25c with first and second portions 27a, 27b, 27c, 29a, 29b, 29c carrying fluid 26a, 26b, 26c, 28a, 28b, 28c; divider 35a, 35b, 35c; and pressure membrane 38a, 38b, 38c. As previously described, aneurysmal pressure is transmitted through the pressure membrane 38a, 38b, 38c and the first fluid 26a, 26b, 26c to position the divider 35a, 35b, 35c within the chamber 25a, 25b, 25c.

As shown in FIG. 2, sensing device 10a may include chamber portions 27a, 29a positioned in a substantially coaxial arrangement (e.g., common longitudinal axes). Furthermore, variations in pressure membrane 38a positioning and chamber 25a geometry are shown. For example, pressure membrane 38a may be positioned adjacent any number of sensing device 10 sides; chamber 25a may have a cubical or cylindrical geometry. Sensing device 10a demonstrates an alternative packaging to device 10.

Sensing device 10b shown in FIG. 3 demonstrates another variation in pressure membrane 38b positioning and chamber 25b geometry. Pressure membrane 38b size may be proportional to the sensitivity of the sensing device. For example, device 10b may have a substantially larger pressure membrane 38b than pressure membrane 38 of device 10 thus providing increased sensitivity. Device 10b may include two markers 37a, 38b spaced at a given distance. The distance may provide a reference during visualization of the device 10b. A divider membrane 40 may be positioned adjacent the compressible fluid (e.g., gas 32a) and liquid second fluid 28b. The divider membrane 40 may function by transmitting aneurysmal pressure from second fluid 28b to compress the compressible fluid.

Figure 4B:
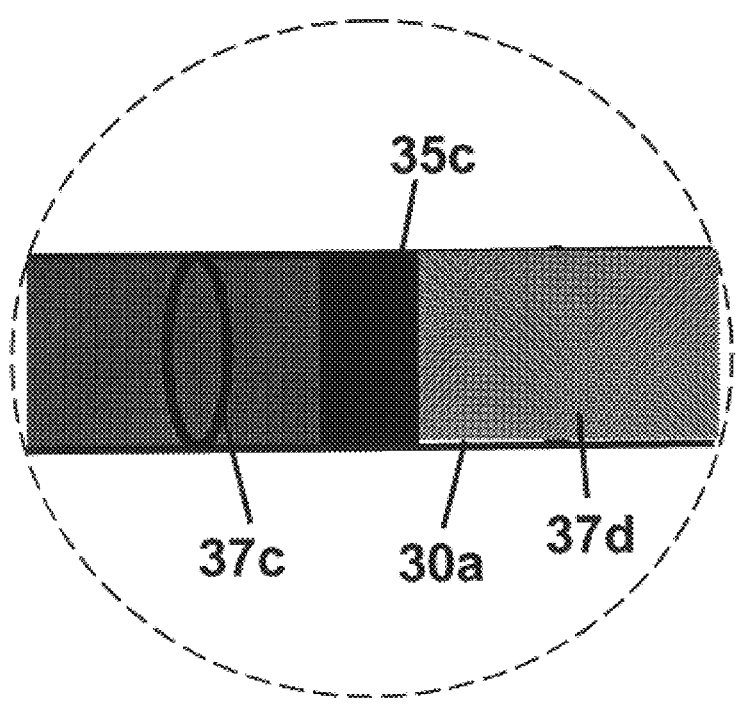
FIG. 4B is a detailed view of a portion of the device shown in FIG. 4A.

As shown in FIG. 4A, device 10c chamber portions 27c, 29c may be separated by an elongated connector portion 30a. As such, device 10c chamber portions 27c, 29c may be positioned remotely from one another. Connector portion 30a (see detailed view FIG. 4B) may include markers 37c, 37d to reference divider 35c movement. Connector portion 30a size may be varied to adjust sensitivity of the sensing device because movement of a unit volume of liquid will impart a greater motion in a smaller tube. For example, device 10c may have a substantially narrower connector portion 30a than the connector portion 30 of device 10 thereby providing increased sensitivity.

Figure 5:
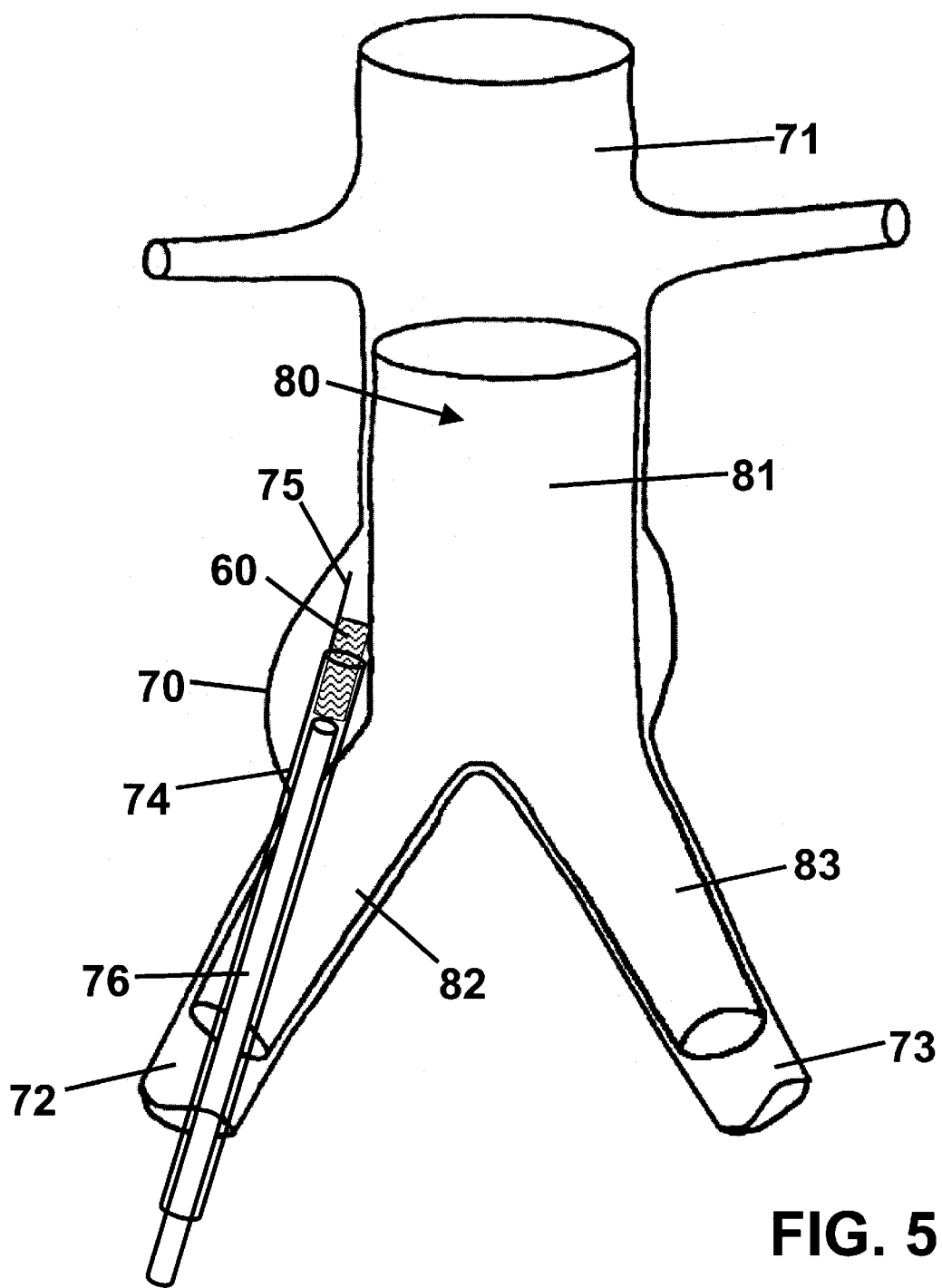
FIG. 5 is a schematic view of a device for sensing aneurysmal pressure being deployed adjacent an abdominal aortic aneurysm and an endoluminal prosthesis, in accordance with the present invention.

Referring now to FIG. 5, a schematic view is provided of a device 60 for sensing aneurysmal pressure being deployed adjacent an abdominal aortic aneurysm 70 and an endoluminal prosthesis 80, in accordance with the present invention. Those skilled in the art will recognize that the sensing device 60 and method for determining aneurysmal pressure are not limited to the described strategy. Numerous modifications, substitutions, and variations may be made to the strategy while effectively determining aneurysmal pressure in a manner consistent with the present invention. For example, the sensing device 60 may be used for aneurysms in body cavities other than the abdominal aorta. In addition, the endoluminal prosthesis 80 may vary as numerous such devices are currently available for aneurysm treatment.

Endoluminal prosthesis 80 may be formed from a variety of materials used for expandable prosthetic devices known in the art. For example, endoluminal prosthesis 80 may include covered stent design elements disclosed in U.S. Pat. No. 6,143,022 issued to Shull et al. Endoluminal prosthesis 80 may further include pleated structure design elements disclosed in U.S. Pat. No. 5,607,464 issued to Trescony el al. In one embodiment, endoluminal prosthesis 80 may be a stent-graft such as the AneuRx® device for endoluminal treatment. Those skilled in the art will recognize that endoluminal prosthesis 80 geometry, size, and construction may vary without diminishing the utility of the present invention. In a presently described embodiment, the endoluminal prosthesis 80 is a bifurcated stent-graft, however, numerous non-bifurcated alternative prosthetic designs may be used with the invention.

Endoluminal prosthesis 80 is shown already deployed in an abdominal aorta 71. Endoluminal prosthesis 80 may be deployed in a vessel by one of many techniques known in the art including intravascular and open surgical methods. Endoluminal prosthesis 80 includes a trunk body 81, a first branch body 82, and second branch body 83. Trunk body 81 includes a relatively large tubular lumen and is deployed in patient abdominal aorta 71. Trunk body 81 lumen bifurcates into smaller branch lumens of the first branch body 82 and second branch body 83. The branch bodies 82, 83 are deployed within first iliac artery 72 and second iliac artery 73. The deployed trunk body 81 and branch bodies 82, 83 preferably seal to each other and to the healthy vascular walls beyond the aneurysm 70 isolating the aneurysm 70 from the bloodstream. Aortic blood flow may enter the trunk body 81 lumen, separate into the two branch portions 82, 83, and then flow into each of the iliac arteries 72, 73 in a path that approximates that of a normal, healthy vascular system.

Determination of aneurysmal pressure may begin with sensing device 60 calibration(s). Calibration may be performed during the design-manufacture of the sensing device 60 or at another advantageous time, such as before deployment. The calibration may include adjusting a radiopaque substance position with respect to a standard pressure before deployment. The radiopaque substance may include the radiopaque fluid and/or divider positioned in the sensing device 60 chamber. In one embodiment, calibration involves positioning the divider with respect to the radiopaque marker. As such, a "baseline" position of the divider may be established before sensing device 60 deployment. In another embodiment, the amount of fluid and/or gas used in the sensing device 60 may be increased or decreased during its manufacture to adjust the fluid and/or divider position as desired.

The calibration may also include adjusting a rate of radiopaque substance movement with respect to the aneurysmal pressure. The rate of substance movement may influence the sensitivity of the device 60. In one embodiment, the size of the pressure membrane, the gas pressure, the geometry and size of the chamber may be adjusted to influence device 60 sensitivity. For example, the geometry and size of the connector portion design may be varied. A connector portion with a smaller diameter may provide increased sensitivity to aneurysm pressure (i.e., divider movement is increased for a given pressure change).

After calibration, the sensing device 60 may be deployed. Sensing device 60 need not have an adjacently deployed prosthesis for function; however, endoluminal prosthesis 80 is included in the present description and figures. Those skilled in the art will recognize that the sensing device 60 may be deployed through numerous pathways (e.g., through alternate iliac arteries 72, 73 or abdominal aorta 71) and methodologies (e.g., flexible catheter or adequate delivery strategy known in the art), however, deployment is demonstrated by catheter 74 through first iliac artery 72. Catheter 74 may be any number of devices used for endoluminal deployment of medical devices known in the art. Delivery of the sensing device 60 may occur after full deployment of the endoluminal prosthesis 80. However, a preferred method involves positioning the sensing device 60 simultaneously with the deployment of the endoluminal prosthesis 80 so that the prosthesis 80 expands against the delivery catheter and seals the sac before the sensing device 60 is deployed.

Sensing device 60 may be positioned within catheter 74 lumen. A guide wire 75 may be positioned into abdominal aorta 71 via patient femoral artery. Catheter 74 may then be advanced through iliac artery 72 and into aneurysm 70 along pre-positioned guide wire 75. Catheter 74 position may be determined by visualization methods known in the art, such as fluoroscopy and/or intravascular ultrasound (IVUS). In one embodiment, radiopaque markers disposed on portion of the catheter 74 may be visualized by fluoroscopy.

After appropriate catheter 74 positioning, sensing device 60 may be deployed. A push rod 76 or other positioning apparatus may be used to place sensing device 60 adjacent the aneurysm 70. In one embodiment, sensing device 60 may be retained adjacent the aneurysm 70 with an anchor (e.g., within vessel wall or on endoluminal prosthesis 80). In another embodiment, sensing device 60 may "float" within aneurysm 70 whereby the endoluminal prosthesis 80 may block egress.

Figure 6:
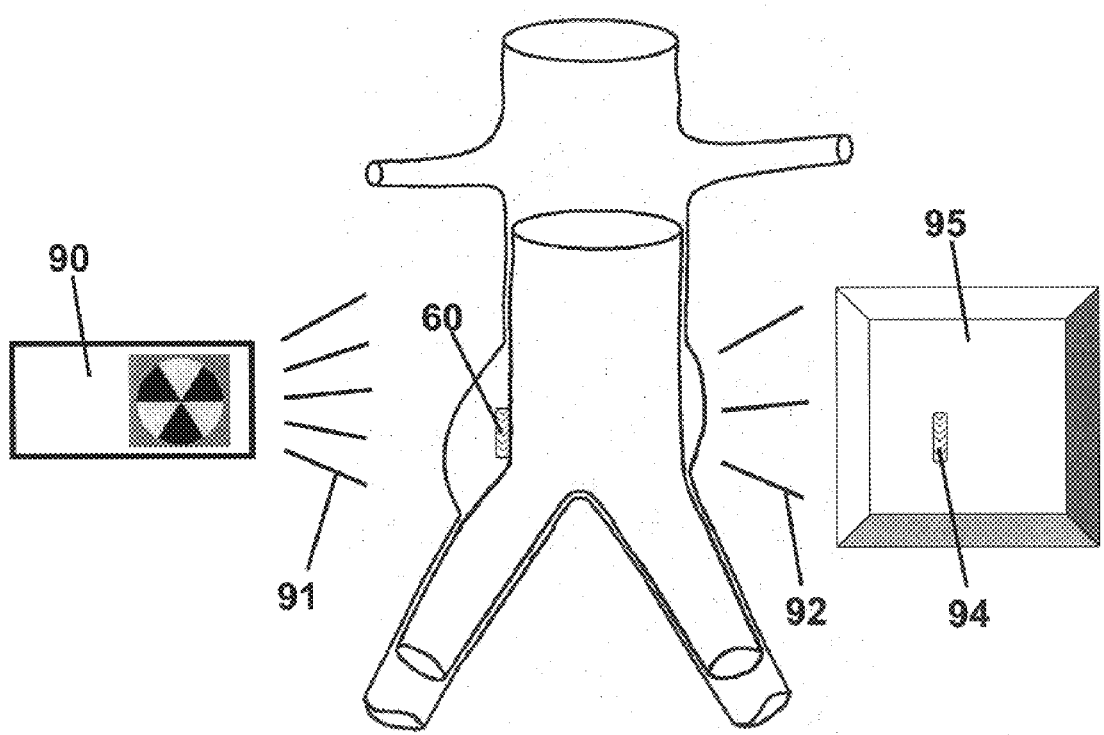
FIG. 6 is a schematic view of a device for sensing aneurysmal pressure being imaged once deployed adjacent an abdominal aortic aneurysm and an endoluminal prosthesis, in accordance with the present invention.

Catheter 74 and guide wire 75 may be removed from patient, leaving sensing device 60 in the deployed state shown in FIG. 6. Sensing device 60 is shown attached to endoluminal prosthesis 80. As the deployed sensing device 60 experiences aneurysmal pressure the radiopaque substance may move through passages in the sensing device 60. In one embodiment, fluid (e.g., radiopaque and/or radiotransparent) moves within the sensing device 60 chamber portions to position the divider (e.g., radiopaque or radiotransparent).

After deployment (e.g., immediately following insertion), the sensing device 60 is imaged. In one embodiment, as shown in FIG. 6, sensing device 60 may be imaged by fluoroscopy. A source 90 may generate electromagnetic radiation 91 that penetrates the patient and deployed radiotransparent materials. Radiopaque materials may absorb and/or deflect the radiation. The penetrating radiation 92 may then be captured on an imaging device 95 to produce a sensing device image 94. The imaging device 95 may include any number of devices for imaging electromagnetic radiation, such as an X-ray film or computerized X-ray detection device. In another embodiment, sensing device 60 may be imaged by other methods known in the art, such as ultrasound. Those skilled in the art will recognize that numerous methods may be used to image the deployed sensing device 60.

After imaging, aneurysmal pressure may be calculated as previously described from sensing device image 94. Further subsequent imaging may reveal a relative change in pressure, which may provide a good indicator of the localized aneurysmal pressure condition. The sensing device 60 provides a strategy for monitoring the aneurysm, specifically through direct measurement of ambient pressure. "Endoleaks" may be detected early as a result of these measurements and aneurysm regrowth may be prevented. The sensing device 60 may also provide the pressure measurements without the need for appreciable volumes of contrast solution. Allergic reactions to theses "dyes" may be minimized or even eliminated.

While the embodiments according to the invention are disclosed herein, various changes and modifications can be made without departing from the spirit and scope of the invention. For example, the sensing device and endoluminal prosthetic configuration, and method of deploying the same are not limited to any particular design or sequence. Specifically, the housing, chamber, fluid, divider, and associated components geometry, size, arrangement, number, material, features, method of calibration, and deployment step order may vary without limiting the utility of the invention.

What is claimed is:

1. A device for sensing aneurysmal pressure in a body cavity, comprising:
   a housing including at least one chamber formed therein;
   a first fluid positioned in a first portion of the chamber;
   a second fluid positioned in a second portion of the chamber;
   a compressible fluid positioned in the second portion of the chamber;
   a divider positioned between the first and second fluids; and
   a pressure membrane in communication with the first portion of the chamber;
   wherein the aneurysmal pressure is transmitted through the membrane and the first fluid to position the divider within the chamber.

2. The device of claim 1 wherein the body cavity is an aorta.

3. The device of claim 1 wherein the first and second fluids are non-miscible.

4. The device of claim 1 wherein at least one of the first and second fluids comprise a biocompatible hydrocarbon.

5. The device of claim 1 wherein at least one of the first and second fluids comprise a radiopaque fluid.

6. The device of claim 5 wherein the radiopaque fluid is selected from a group consisting of barium sulfate, diatrizoate, iodipamide, iohexol, iopamidol, iothalamate, ioversol, ioxaglate, and metrizamide.

7. The device of claim 1 wherein the divider is manufactured from a radiopaque material.

8. The device of claim 7 wherein the radiopaque material is selected from a group consisting of gold, silver, tantalum oxide, tantalum, platinum, platinum/iridium alloy, and tungsten.

9. The device of claim 1 further comprising an anchor portion operably attached to the housing, wherein the anchor retains the housing adjacent the aneurysm.

10. The device of claim 1 further comprising at least one gas positioned in the chamber, wherein the gas volume changes in response to the aneurysmal pressure.

11. The device of claim 1 further comprising at least one radiopaque marker disposed on the housing.

12. The device of claim 1 further comprising an endoluminal prosthesis positioned adjacent the aneurysm.

13. The device of claim 1 further comprising a divider membrane positioned adjacent the compressible fluid and the second fluid wherein the second fluid is a liquid.

14. A method for determining aneurysmal pressure in a body cavity, comprising:
   deploying a sensing device including radiopaque substance adjacent an aneurysm;
   moving the radiopaque substance within the device in response to the aneurysmal pressure; and
   imaging the sensing device.

15. The method of claim 14 wherein the body cavity is an aorta.

16. The method of claim 14 wherein deploying the sensing device comprises catheter deployment.

17. The method of claim 14 wherein deploying the sensing device comprises retaining the sensing device adjacent the aneurysm.

18. The method of claim 14 wherein imaging the sensing device comprises fluoroscopic imaging.

19. The method of claim 14 further comprising calibrating the sensing device.

20. The method of claim 19 wherein calibrating the sensing device comprises adjusting a radiopaque substance position with respect to a standard pressure before deployment.

21. The method of claim 19 wherein calibrating the sensing device comprises adjusting a rate of radiopaque substance movement with respect to the aneurysmal pressure.

22. The method of claim 19 further comprising deploying an endoluminal prosthesis adjacent the aneurysm.

* * * * *